United States Patent [19]

Sakashita et al.

[11] Patent Number: 5,391,539
[45] Date of Patent: Feb. 21, 1995

[54] HERBICIDAL COMPOSITION COMPRISING GLUFOSINATE AND A HETEROCYCLIC SULFONYLUREA HERBICIDE

[75] Inventors: Nobuyuki Sakashita; Hiroshi Yoshii; Tsunezo Yoshida; Shooichi Honzawa; Hiroshi Kikugawa, all of Shiga, Japan

[73] Assignee: Ishihara Sangyo Kaisha, Ltd., Osaka, Japan

[21] Appl. No.: 161,060

[22] Filed: Dec. 3, 1993

Related U.S. Application Data

[63] Continuation of Ser. No. 903,446, Jun. 24, 1992, abandoned, which is a continuation-in-part of Ser. No. 718,463, Jun. 20, 1991, abandoned.

[30] Foreign Application Priority Data

Jun. 20, 1990 [JP] Japan ................... 2-162191
Mar. 26, 1991 [JP] Japan ................... 3-132444

[51] Int. Cl.$^6$ ............... A01N 57/04; A01N 43/54
[52] U.S. Cl. ............................ 504/128
[58] Field of Search .......................... 504/128

[56] References Cited

U.S. PATENT DOCUMENTS

| | | | |
|---|---|---|---|
| 4,168,963 | 9/1979 | Rupp et al. | 71/86 |
| 4,435,206 | 3/1984 | Levitt | 71/92 |
| 4,744,814 | 5/1988 | Kimura et al. | 71/92 |
| 5,173,103 | 12/1992 | Yoshida et al. | 71/86 |

FOREIGN PATENT DOCUMENTS 0252237 1/1988 European Pat. Off. .

*Primary Examiner*—Richard L. Raymond
*Assistant Examiner*—S. Mark Clardy
*Attorney, Agent, or Firm*—Sughrue, Mion, Zinn, Macpeak & Seas

[57] ABSTRACT

A herbicidal composition is disclosed, comprising, as active ingredients, 1-(4,6-dimethoxypyrimidin-2-yl)-3-(3-trifluoromethyl-2-pyridylsulfonyl)urea and an ammoium salf of homoalanin-4-yl(methyl)phosphinic acid.

7 Claims, No Drawings

HERBICIDAL COMPOSITION COMPRISING GLUFOSINATE AND A HETEROCYCLIC SULFONYLUREA HERBICIDE

CROSS REFERENCE TO RELATED APPLICATION

This is a Continuation of Application No. 07/903,446 filed Jun. 24, 1992, now abandoned, which is a Continuation-in-Part of Application No. 07/718,463 filed Jun. 20, 1991, now abandoned.

FIELD OF THE INVENTION

The present invention relates to a herbicidal composition comprising, as active ingredients, 1-(4,6-dimethoxy-pyrimidin-2-yl)-3-(3-trifluoromethyl-2-pyridylsulfonyl) urea (hereinafter referred to as "Compound A") and an ammonium salt of homoalanin-4-yl(methyl)-phosphinic acid (hereinafter referred to as "Compound B").

BACKGROUND OF THE INVENTION

Many kinds of herbicides have been developed and are used nowadays. Since objects for control with a herbicide include a wide variety of weeds with a long duration of emergence, there has been a demand for development of a herbicide having a wider herbicidal spectrum, a high activity and a persistent herbicidal effect.

As a result of extensive investigations with a view to developing a herbicide with characteristics as mentioned above, the inventors of the present invention have found out that the herbicidal composition of the present invention can control a wide variety of weeds emerging in crop lands as well as non-crop lands. More specifically, it has been found out that the herbicidal effect of the herbicidal composition of the present invention is unexpectedly higher than the mere addition of the herbicidal effects of individual active ingredients and, in short, is manifested as a synergistic herbicidal effect, whereby the herbicidal composition of the present invention may be applied in smaller amounts of the active ingredients with an expanded herbicidal spectrum and a persistent herbicidal effect as compared with any one of the individual active ingredients when singly applied. Thus, the present invention has been completed.

SUMMARY OF THE INVENTION

An object of the present invention is to provide a herbicidal composition comprising, as active ingredients, Compound A and an ammonium salt of Compound B.

DETAILED DESCRIPTION OF THE INVENTION

The ammonium salt of Compound B as one of the active ingredients usable in the herbicidal composition of the present invention encompasses ammonium salts of optical isomers of Compound B inclusive of those of D,L-homoalanin-4-yl(methyl)phosphinic acid (common name: D,L-glufosinate, hereinafter referred to as "D,L-isomer of Compound B") and L-homoalanin-4-yl(methyl)phosphinic acid (common name: L-glufosinate, hereinafter referred to as "L-isomer of Compound B").

The amount of the ammonium salt of Compound B as one of the active ingredients of the herbicidal composition of the present invention, relative to the amount of Compound A as another active ingredient to be mixed therewith, may be in a comparatively wide range. However, the amount of the ammonium salt of Compound B is usually from 0.3 to 80 parts by weight, preferably from 2.5 to 40 parts by weight, and more preferably from 5 to 30 parts by weight, per part by weight of Compound A.

The amount of application of the herbicidal composition of the present invention cannot be unequivocally defined because it varies depending on the mixing ratio of the active ingredients, the type of formulation, the kind of object weed, the weather condition, etc. However, it is usually employed such that from 0.05 to 5 g, and preferably from 0.2 to 3 g, per are (are (a) = 100 m$^2$), of Compound A is used in combination with from 0.3 to 30 g, and preferably from 2.5 to 15 g, per are, of the ammonium salt of Compound B, with a total amount of the active ingredients being from 0.35 to 35 g, and preferably from 2.5 to 18 g, per are. Where the herbicidal composition of the present invention is applied after being diluted with water, an adjuvant(s) such as a spreader may be additionally used, if desired.

Respective active ingredients are often found to exhibit a defect in terms of the herbicidal activity when applied singly. However, there may be a case that when two kinds of active ingredients are applied in combination, the resulting herbicidal activity is higher than one obtained by simply summing up the activity of each of the two active ingredients (i.e., an expected activity). In such a case, it is said that a synergistic action is found. The expected activity which is brought by a specific combination of two kinds of herbicides can be calculated by the following equation as described, for example, in S. R. Colby, *Weeds*, "Calculating Synergistic and Antagonistic Responses of Herbicide Combinations", Vol. 15, pp. 20–22 (1967).

$$E = \alpha + \beta - \frac{\alpha \times \beta}{100}$$

In the above equation, $\alpha$ represents a growth inhibition rate (%) when treated with a (g/are) of herbicide A; $\beta$ represents a growth inhibition rate (%) when treated with b (g/are) of herbicide B; and E represents an expected growth inhibition rate (%) when treated with a (g/are) of herbicide A and b (g/are) of herbicide B.

That is, if an actual growth inhibition rate (found value) is higher than the growth inhibition rate (calculated value) by the above-mentioned calculation, it can be said that the activity brought by the combination of herbicides exhibits a synergistic action.

The herbicidal composition of the present invention is extremely high in usefulness so that it completely exterminates a wide variety of weeds ranging from annual weeds to perennial weeds even when used in small amounts of the active ingredients. Also, when applied at the time of either pre-emergence or post-emergence of weeds, it is effective so that it can exhibit a high level of herbicidal effect when used according to either soil treatment application or foliage treatment application. Therefore, the herbicidal composition of the present invention is useful for control of weeds not only in the agricultural and horticultural fields involving upland fields, orchards, etc., but also in non-crop lands including playgrounds, vacant lots, forests, and tank yards (areas of storage tanks).

The herbicidal composition of the present invention is prepared by blending various adjuvants with Compound A and the ammonium salt of Compound B into a formulation such as a wettable powder, a suspension concentrate, a water-dispersible granule, a granule, a dust, a water-soluble granule, a water-soluble powder, or a soluble concentrate according to any customary method of preparing agricultural chemicals. Compound A and the ammonium ssalt of Compound B may be either mixed together and prepared into a formulation, or prepared into separate formulations and mixed together.

The above-mentioned formulations of the herbicidal composition of the present invention may contain from 1 to 98%, and preferably from 2 to 95%, in terms of weight ratio, of the active ingredients.

Examples of the above-mentioned adjuvants include solid carriers such as diatomaceous earth, slaked lime, calcium carbonate, talc, white carbon, kaolin, bentonite, zieclite, water-soluble starch, sodium carbonate, sodium bicarbonate, and sodium sulfate; antifreezing agents such as ethylene glycol and propylene glycol; spreaders and surfactants such as salts of alkyl sulfates, salts of alkylbenzenesulfonates, salts of lignosulfonate, polyoxyethylene glycol alkyl ethers, polyoxyethylene lauryl ethers, polyoxyethylene alkylaryl ethers, polyoxyethylene fatty acid esters, polyoxyethylene sorbitan fatty acid esters, polyoxyethylene styrylphenyl ethers, salts of polycarboxylates, salts of dialkyl sulfosuccinates, salts of alkyl diglycol ether sulfates, salts of polyoxyethylene alkylaryl ether sulfates, salts of polyoxyethylene alkylaryl phosphates, polyoxyethylene hydrogenated castor oil, salts of styrylphenyl phosphate, and condensates of salts of napthalene-sulfonate and formalin; crop oils and mineral oils such as olive oil, kapok oil, castor oil, papaya oil, camellia oil, coconut oil, sesame oil, corn oil, rice bran oil, peanut oil, cotton seed oil, soybean oil, rape seed oil, linseed oil, tung oil, and liquid paraffin; solvents such as propylene glycol monomethyl ether; thixotropic materials such as aluminum magnesium silicate and bentonite-alkylamino complexes; and thickeners such as xanthangum. The above-mentioned adjuvants may be used in a preliminarily mixed form thereof, if desired. The herbicidal composition of the present invention, prepared in the foregoing manner, may further comprise other herbicides, insecticides, fungicides, and/or plant growth regulators incorporated thereinto.

A description will now be made of Formulation Examples of the herbicidal composition of the present invention, which are, however, not restrictive.

Formulation Example 1

| (1) | Ammonium salt of D,L-isomer of Compound B | 50 parts by weight |
|---|---|---|
| (2) | Compound A | 10 parts by weight |
| (3) | Mixture of sodium dioctyl sulfosuccinate and sodium benzoate (New Kalgen EX-70 ®, manufactured by Takemoto Oil & Fat Co., Ltd.) | 20 parts by weight |
| (4) | Ammonium chloride | 20 parts by weight |

The above-mentioned components are mixed together to obtain a wettable powder.

Formulation Example 2

| (1) | Ammonium salt of D,L-isomer of Compound B | 30 parts by weight |
|---|---|---|
| (2) | Compound A | 2 parts by weight |
| (3) | Soybean oil | 54 parts by weight |
| (4) | Bentonite-alkylamino complex (New D Orben ®: manufactured by Shiraishi Kogyo Kaisha, Ltd.) | 2 parts by weight |
| (5) | Mixture of a polyoxyethylene alkylaryl ether, a polyoxyethylene hydrogenated castor oil, a polyoxyethylene alkylaryl phosphate, a sodium dialkyl sulfosuccinate and a polyoxyethylene fatty acid ester (Sorpol 3747K ®: manufactured by Toho Chemical Industry Co., Ltd.) | 12 parts by weight |

The above-mentioned components are uniformly mixed together by a wet pulverizer to obtain an oil-based suspension concentrate.

Formulation Example 3

| (1) | Ammonium salt of D,L-isomer of Compound B | 30 parts by weight |
|---|---|---|
| (2) | Compound A | 2 parts by weight |
| (3) | Liquid normal paraffin | 51 parts by weight |
| (4) | Bentonite-alkylamino complex (New D Orben ®) | 2 parts by weight |
| (5) | Polyoxyethylene sorbitan trioleate (Sorbon T-85 ®: manufactured by Toho Chemical Industry Co., Ltd.) | 15 parts by weight |

The above-mentioned components are uniformly mixed together by a wet pulverizer to obtain an oil-based suspension concentrate.

Formulation Example 4

| (1) | Ammonium salt of L-isomer of Compound B | 30 parts by weight |
|---|---|---|
| (2) | Compound A | 2 parts by weight |
| (3) | Zieclite | 51 parts by weight |
| (4) | Condensate of sodium naphthalene-sulfonate and formalin (Lavelin S ®: manufactured by Dai-ichi Kogyo Seiyaku Co., Ltd.) | 2 parts by weight |
| (5) | White carbon | 10 parts by weight |
| (6) | Sodium polyoxyethylene alkylaryl ether sulfate-premix with white carbon (Sorpol 5039 ®: manufactured by Toho Chemical Industry Co., Ltd.) | 5 parts by weight |

The above-mentioned components are mixed together to obtain a wettable powder.

Formulation Example 5

| (1) | Ammonium salt of D,L-isomer of Compound B | 80 parts by weight |
|---|---|---|
| (2) | Compound A | 5 parts by weight |
| (3) | Surfactant of special polycarboxylic acid type polymer (Demol EPO ®: manufactured by Kao Corporation) | 8 parts by weight |
| (4) | Sodium sulfate | 7 parts by weight |

The above-mentioned components are dissolved or suspended in a three-fold amount of water and dried by a spray dryer to obtain a water-dispersible granule.

Formulation Example 6

| | | |
|---|---|---|
| (1) | Ammonium salt of D,L-isomer of Compound B | 75 parts by weight |
| (2) | Compound A | 2.5 parts by weight |
| (3) | Sodium alkyl sulfate (Monogen Y-5000 ®: manufactured by Dai-ichi Kogyo Seiyaku Co., Ltd.) | 10 parts by weight |
| (4) | Sodium sulfate | 12.5 parts by weight |

The above-mentioned components are mixed together to obtain a wettable powder.

Formulation Example 7

| | | |
|---|---|---|
| (1) | Ammonium salt of D,L-isomer of Compound B | 2 parts by weight |
| (2) | Compound A | 0.2 parts by weight |
| (3) | Calcium carbonate (fine granules) | 92.8 parts by weight |
| (4) | Sodium dialkyl sulfosuccinate (Neocol YSK ®: manufactured by Dai-ichi Kogyo Seiyaku Co., Ltd.) | 1 part by weight |
| (5) | Polyoxyethylene octylphenyl ether (Noigen EA-92 ®: manufactured by Dai-ichi Kogyo Seiyaku Co., Ltd.) | 2 parts by weight |
| (6) | White carbon | 2 parts by weight |

The above-mentioned components are mixed together to obtain a granule.

Formulation Example 8

| | | |
|---|---|---|
| (1) | Ammonium salt of D,L-isomer of Compound B | 89 parts by weight |
| (2) | Compound A | 6 parts by weight |
| (3) | Condensate of sodium naphthalenesulfonate and formalin (Lavelin FAN ®:) | 5 parts by weight |

The above-mentioned components are mixed together to obtain a wettable powder.

Formulation Example 9

| | | |
|---|---|---|
| (1) | Amonium salt of D,L-isomer of compound B | 82.5 parts by weight |
| (2) | Compound A | 5.5 parts by weight |
| (3) | Sodium bicarbonate | 7 parts by weight |
| (4) | Sodium alkyl sulfate (Monogen Y-500 ®:) | 5 parts by weight |

The above-mentioned components are mixed together to obtain a water-soluble powder.

Formulation Example 10

| | | |
|---|---|---|
| (1) | Ammonium salt of D,L-isomer of Compound B | 60 parts by weight |
| (2) | Compound A | 4 parts by weight |
| (3) | Sodium alkyl sulfate (Monogen Y-500 ®) | 15 parts by weight |
| (4) | Calcium lignosulfonate | 10 parts by weight |
| (5) | Sodium sulfate | 11 parts by weight |

The above-mentioned components are mixed together to obtain a wettable powder.

The herbicidal effect of the herbicidal composition of the present invention will now be demonstrated in the following Test Examples.

Test Example 1 (Foliage Treatment Test)

Upland soil was placed in 1/5000—are (are (a)=100 m$^2$) wagner pots and planted with hills of *Solidago altissima* collected in the fields, and the hills were thereafter grown in a greenhouse. When the plant height reached 20 to 30 cm, a predetermined amount of each herbicidal composition which had been diluted with 15 l, per are, of water and further admixed with 0.05% (v/v) of a spreader (Shin Rino ®: manufactured by Nihon Nohyaku Co., Ltd.) was foliarly applied on the plants using a small spray gun. 25 days after the foliage treatment application, the fresh weight of foliage was measured. The above plant test was conducted at the same time under the same conditions. The growth inhibition rate (%), which is listed in Table 1, was calculated according to the following equation (found value):

$$\text{Growth Inhibition Rate (\%)} = \left(1 - \frac{\text{Fresh Weight of Foliage in Treated Plot}}{\text{Fresh Weight of Foliage in Untreated Plot}}\right) \times 100$$

In addition, the growth inhibition rate (%) calculated by the above-cited Colby equation (calcuated value) is also listed in Table 1.

TABLE 1

| | Amount of Application of Active Ingredients (g/a) | Growth Inhibition Rate (%) | |
|---|---|---|---|
| | | Found | Calculated |
| Compound A | 1 | 63 | |
| | 0.5 | 51 | |
| | 0.25 | 46 | |
| Ammonium salt of D,L-isomer of Compound B (commercial name: Basta) | 10 | 84 | |
| | 5 | 72 | |
| | 2.5 | 55 | |
| Compound A + Ammonium salt of D,L-isomer of Compound B (commercial name: Basta) | 1 + 10 | 100 | 94 |
| | 1 + 5 | 100 | 90 |
| | 1 + 2.5 | 100 | 83 |
| | 0.5 + 10 | 100 | 92 |
| | 0.5 + 5 | 100 | 86 |
| | 0.5 + 2.5 | 88 | 78 |
| | 0.25 + 10 | 97 | 91 |
| | 0.25 + 5 | 94 | 85 |
| | 0.25 + 2.5 | 85 | 76 |

Test Example 2 (Foliage Treatment Test)

Upland soil was placed in 1/10000—are pots and sown with *Digitaria sanguinalis*. When the plants reached the four-leaf stage, a predetermined amount of each herbicidal composition which had been diluted with 15 l, per are, of water and further admixed with 0.2% (v/v) of a spreader (Shin Rino ®) was foliarly applied on the plants using a small spray gun. 20 days after the foliage treatment application, the fresh weight of the aerial part of the plant was measured. The above plant test was conducted at the same time under the same conditions. The growth inhibition rate (%) calculated by the equation given in Test Example 1 (found value) and the growth inhibition rate (%) calculated by the above-cited Colby equation (calculated value) are listed in Table 2.

TABLE 2

| | Amount of Application of Active Ingredients (g/a) | Growth Inhibition Rate (%) | |
|---|---|---|---|
| | | Found | Calculated |
| Compound A | 5 | 99.4 | |
| | 1 | 67.3 | |
| | 0.6 | 47.4 | |
| | 0.4 | 16.9 | |
| | 0.2 | 5.3 | |
| | 0.1 | 3.5 | |
| | 0.05 | 0 | |
| Ammonium salt of D,L-isomer of Compound B (commercial name: Basta) | 10 | 100 | |
| | 5 | 94 | |
| | 3 | 85 | |
| | 2 | 52.3 | |
| | 1 | 35.8 | |
| | 0.5 | 12.8 | |
| | 0.3 | 0.9 | |
| Compound A + Ammonium salt of D,L-isomer of Compound B (commercial name: Basta) | 1 + 0.5 | 99.4 | 71.5 |
| | 1 + 0.3 | 90.3 | 67.6 |
| | 0.6 + 0.5 | 95.0 | 54.1 |
| | 0.6 + 0.3 | 96.3 | 47.9 |
| | 0.4 + 0.5 | 95.7 | 27.5 |
| | 0.4 + 0.3 | 91.9 | 17.6 |
| | 0.2 + 4 | 96.9 | 90.5 |
| | 0.2 + 3 | 95.4 | 85.8 |
| | 0.2 + 2 | 86.9 | 54.8 |
| | 0.2 + 1 | 81.3 | 39.2 |
| | 0.2 + 0.5 | 78.8 | 17.4 |
| | 0.2 + 0.3 | 72.3 | 6.2 |
| | 0.1 + 4 | 97.2 | 90.4 |
| | 0.1 + 3 | 87.2 | 85.5 |
| | 0.1 + 2 | 75.4 | 54.0 |
| | 0.1 + 1 | 74.1 | 38.0 |
| | 0.1 + 0.5 | 72.3 | 15.9 |
| | 0.1 + 0.3 | 62.0 | 4.4 |
| | 0.05 + 4 | 96.6 | 90.0 |
| | 0.05 + 3 | 89.7 | 85.0 |
| | 0.05 + 2 | 72.0 | 52.3 |
| | 0.05 + 1 | 70.4 | 35.8 |
| | 0.05 + 0.5 | 70.4 | 12.8 |
| | 0.05 + 0.3 | 57.0 | 0.9 |

Test Example 3 (Foliage Treatment Test)

Upland soil was placed in 1/10000—are pots and sown with Digitaria sanguinalis. When the plants reached the four-leaf stage, a predetermined amount of each herbicidal composition which had been diluted with 15 l, per are, of water and further admixed with 0.2% (v/v) of a spreader (Shin Rino ®) Was foliarly applied on the plants using a small spray gun. 21 days after the foliage treatment application, the fresh weight of the aerial part of the plant was measured. The above plant test was conducted at the same time under the same conditions. The growth inhibition rate (%) calculated by the equation given in Test Example 1 (found value) and the growth inhibition rate (%) calculated by the above-cited Colby equation (calculate value) are listed in Table 3.

TABLE 3

| | Amount of Application of Active Ingredients (g/a) | Growth Inhibition Rate (%) | |
|---|---|---|---|
| | | Found | Calculated |
| Compound A | 1 | 68 | |
| | 0.5 | 28 | |
| | 0.1 | 9 | |
| Ammonium salt of D,L-isomer of Compound B (commercial name: Basta) | 1 | 35 | |
| | 0.9 | 29 | |
| | 0.5 | 14 | |
| | 0.4 | 8 | |
| Compound A + Ammonium salt of D,L-isomer of Compound B (commercial name: Basta) | 0.1 + 0.4 | 69 | 16 |
| | 0.1 + 0.9 | 74 | 35 |

While the invention has been described in detail and with reference to specific embodiments thereof, it will be apparent to one skilled in the art that various changes and modifications can be made therein without departing from the spirit and scope thereof.

What is claimed is:

1. A herbicidal composition comprising, as active ingredients, 1-(4,6-dimethoxypyrimidin-2-yl)-3-(3-trifluoromethyl-2-pyridylsulfonyl)urea and an ammonium salt of homoalanin-4-yl(methyl)phosphinic acid in a weight ratio of from 1:0.3 to 1:80.

2. The herbicidal composition according to claim 1, wherein said composition is adapted to apply from 0.05 to 5 g, per are, of 1-(4,6-dimethoxypyrimidin-2-yl)-3-(3-trifluoromethyl-2-pyridylsulfonyl)urea in combination with from 0.3 to 30 g, per are, of the ammonium salt of homoalanin-4-yl(methyl)phosphinic acid, with the total amount of the two active ingredients being from 0.35 to 35 g per are.

3. The herbicidal composition according to claim 1, wherein the weight ratio of 1-(4,6-dimethoxypyrimidin-2-yl)-3-(3-trifluoromethyl-2-pyridylsulfonyl)urea to the ammonium salt of homoalanin-4-yl(methyl)phosphinic acid is in a range of from 1:5 to 1:30.

4. The herbicidal composition according to claim 1, wherein the herbicidal composition is adapted to be applied to an area where at least one of Solidago altissima and Digitaria sanguinalis grows.

5. The herbicidal composition according to claim 1, wherein the weight ratio of 1-(4,6-dimethoxypyrimidin-2-yl)-3-(3-trifluoromethyl-2-pyridylsulfonyl)urea to the ammonium salt of homoalanin-4-yl(methyl)phosphinic acid is in a range of from 1:2.5 to 1:40.

6. The herbicidal composition according to claim 1, wherein said composition is adapted to apply from 0.2 to 3 g, per are, of 1-(4,6-dimethoxypyrimidin-2-yl)-3-(3-trifluoromethyl-2-pyridylsulfonyl)urea in combination with from 2.5 to 15 g, per are, of the ammonium salt of homoalanin-4-yl(methyl)phosphinic acid, with the total amount of the two active ingredients being from 2.5 to 18 g per are.

7. The herbicidal composition according to claim 6, wherein the herbicidal composition is adapted to be applied to an area where at least one of Solidago altissima and Digitaria sanguinalis grows.

* * * * *